US005395764A

United States Patent [19]
Riboli et al.

[11] Patent Number: 5,395,764
[45] Date of Patent: Mar. 7, 1995

[54] PROMOTER OF THE GENE WHICH CODES FOR THE PILINIC SUBUNIT FIM3 OF BORDETELLA PERTUSSIS AND ITS USE FOR THE EXPRESSION IN BORDETELLA OF THE GENES WHICH CODE FOR A PROTEIN OF INTEREST

[75] Inventors: Barbara Riboli, Cremona; Paola Pedroni, Milan; Anna Cuzzoni, Pavia; Francesca de Ferra, San Donato Milanese; Guido Grandi, Segrate - San Felice, all of Italy

[73] Assignee: Eniricerhce S.p.A., Milan, Italy

[21] Appl. No.: 213,811

[22] Filed: Mar. 16, 1994

Related U.S. Application Data

[63] Continuation of Ser. No. 607,966, Oct. 31, 1990, abandoned.

[30] Foreign Application Priority Data

Nov. 3, 1989 [IT] Italy ................................. 22252/89

[51] Int. Cl.⁶ .................. C12N 1/21; C12N 15/11; C12N 15/31; C12N 15/74
[52] U.S. Cl. .................. 435/252.3; 435/320.1; 536/23.2; 536/23.7; 536/24.1
[58] Field of Search .................. 435/252.3, 320.1; 536/23.2, 23.7, 24.1

[56] References Cited

U.S. PATENT DOCUMENTS

| 4,338,299 | 7/1982 | Vesselinova | 424/254.1 |
| 4,770,875 | 9/1988 | Kume et al. | 424/253.1 |
| 5,059,537 | 10/1991 | Pedroni et al. | 435/252.31 |

FOREIGN PATENT DOCUMENTS 0324124  7/1989  European Pat. Off. ...... C12N 15/00

OTHER PUBLICATIONS

Suzuki et al. (1986), An Introduction to Genetic Analysis, Third Edition (W. H. Freeman & Co., New York), pp. 315–316.

Mooi et al., FEMS Micro Lett., 66:327–332 (1990).
Willems et al., EMBO J., 9(9):2803–2809 (1990).
Pedroni et al., Mol. Micro., 2(4):539–543 (1988).
Gross et al., Proc. Natl. Acad. Sci. USA 85:3913–3917 (1988).
Livey et al., Mol. Micro. 1:203–209 (1987).
Mooi., et al., Microbial Pathogenesis 2:473–484 (1987).
Shimuzu et al. Infect. Immuno., 36(1):198–201 (1982).
Mooi, Antonie Van Leeuwenhoek, 54(5):465–474 (1988).
Molecular Microbiology, vol. 4, No. 1, 1990, p. 3947; M. J. Walker et al.: "Engineering upstream transcriptional and translational signals of Bordetella pertussis serotype 2 fimbrial subunit protein for efficient expression in Escherichia coli: in vitro autoassembly of the expressed product into filamentous structures".

(List continued on next page.)

Primary Examiner—Richard A. Schwartz
Assistant Examiner—Philip W. Carter
Attorney, Agent, or Firm—Sughrue, Mion, Zinn, Macpeak & Seas

[57] ABSTRACT

The isolation and characterization of the promoter regions of the genes which code for the pilinic subunits fim2, fim3 and fimx of Bordetella pertussis, are described, as well as the construction of vectors containing the regions, and microorganisms transformed by the vectors.

The promoter regions, or nucleotide fragments thereof, are particularly useful for the regulable or non-regulable expression of genes which code for a protein of interest in a strain of Bordetella. The transformed Bordetella strains are particularly suitable for the development of an effective anti-pertussis vaccine.

11 Claims, 8 Drawing Sheets

PROMOTER REGION OF THE GENE FIM2

| CTGCAGGCCT | ACCCGGACAG | CACGCTCAAG | GGTCGCGCCA | ACCTGCTGGT | CATGCCCAAC | 60 |
| CTCGATACCG | GCAACATCAC | CTACAACATG | CTGAAGATGA | CCGGCAGCAA | CGGGATTCGA | 120 |
| TGGGCCCGAT | CCTGCTGGGT | TCGGCCCGCC | CGGTGCACAT | CCTGACCACC | AGCGCCACCG | 180 |
| TGCGCCGCAT | CGTCAACATG | ACGGCATTGG | CATGGTGGAC | GCGCAGCAGG | AAGCCGCCGA | 240 |
| AGGCTGACGC | TGATGCGCCG | GCCCGGCGCC | GCCATGGCGC | CGGGCCCTGC | ATGCACGGGT | 300 |
| CCAGTCCCGA | TAAAGCCGC   | ATGCAAAAGG | ACTGTTTCCC | ACATCGGAAT | CAGCCCCCCC | 360 |
| CCCCCCCCT  | AAGACCTAAG | ATCGTGGCTC | CATAACTCTT | CTGGCGCCAA | GACGCCCGTG | 420 |
| TTACCCATG  |            |            |            |            |            | 429 |

OTHER PUBLICATIONS

Weiss et al, "Virulence Factors of *Bordetella Pertussis*", *Ann. Rev. Microbiol.*, 40:661–686 (1986).

Gross et al, "Pertussis Toxin Promoter Sequences Involved in Modulation", *Journal of Bacteriology*, 171(7):4026–4030 (1989).

Weiss et al, "Tn5-Induced Mutations Affecting Virulence Factors of *Bordetella Pertussis*", *Infection and Immunity*, 42(1):33–41 (1983).

Weiss et al, "Genetic Analysis of Phase Change in *Bordetella Pertussis*", *Infection and Immunity*, 43(1):263–269 (1984).

Riboli et al, "Expression of *Bordetella Pertussis* Fimbrial (fim) genes in *Bordetella Bronchiseptica*: fixX is Expressed at a Low Level and vir-regulated", *Microbial. Pathogenesis.*, 10:393–403 (1991).

Gentz et al, "Cloning and Analysis of Strong Promoters is Made Possible by the Downstream Placement of a RNA Termination Signal", *Proc. Natl. Acad. Sci. USA,* 78(8):4936–4940 (1981).

Flock et al, "Expression in *Bacillus Subtilis* of the Gene for Human Urogastrone Using Synthetic Ribosome Binding Sites", *Mol. Gen. Genet.,* 195:246–251 (1984).

PROMOTER REGION OF THE GENE FIM2

| CTGCAGGCCT | ACCCGGACAG | CACGCTCAAG | GGTCGGGCCA | ACCTGCTGGT | CATGCCCAAC | 60 |
| CTCGATACCG | GCAACATCAC | CTACAACATG | CTGAAGATGA | CCGGCAGCAA | CGGGATTCGA | 120 |
| TGGGCCCGAT | CCTGCTGGGT | TCGGCCCGCC | CGGTGCACAT | CCTGACCACC | AGCGCCACCG | 180 |
| TGCGCCCGAT | CGTCAACATG | ACGGCATTGG | CATGGTGGAC | GCGCAGCAGG | AAGCCGGCGA | 240 |
| AGGCTGACGC | TGATGCGCCG | GCCCGGGCGC | GCCATGGGCG | CGGGCCCTGC | ATGCACGGGT | 300 |
| CCAGTCCCGA | TAAAAGCCGC | ATGCAAAAGG | ACTGTTTCCC | ACATCGGAAT | CAGCCCCCCC | 360 |
| CCCCCCCCCT | AAGACCTAAG | ATCGTGGCTC | CATAACTCTT | CTGGCGCCAA | GACGCCCGTG | 420 |
| TTACCCATG | | | | | | 429 |

FIG. 1a

PROMOTER REGION OF THE GENE FIMX

| | | | | | |
|---|---|---|---|---|---|
| GCGGGCAGACG | CTGGCGGCGC | TGCTGGGCGA | AGTGCTCAAC | CTGCTCGGGC | GCACAGGCCT | 60
| TCGGGCTGCG | GTGCGGGGCA | GAACTGCGGT | CAAGCAGGCC | GTCCAGACCT | TCGCTTCGGA | 120
| AGCGGGCAAG | CCACTTGTAA | CCGGTGCGCA | GGCTGCACCC | CTGCGCGCCT | GCTGGCCTGG | 180
| CCTCATCGTC | CAGTTCTGTT | GCATCACCCT | GTTAACAAGA | AGGGCTCGAC | CTAGGCGGGT | 240
| CAATCGGCA | TGCTTATGGT | TGTTCATCCA | GTGTCCTGCC | CTGAGTTGCG | ATGGCGTGGT | 300
| AACCACAGCA | TCCCAGGTCC | GGCCTGGATG | AACAACCTAT | TGAGACATCA | CACCTAGCGG | 360
| GGCGAATGCG | CGGATATCGA | GGCAGCTTGG | GCCAAATCCC | ATAAGCTGAC | GAACCCGCCC | 420
| CTCGATGGCA | GCCCAAACCC | TTACAACATA | AGTGGTTCCC | GCCGTCGTCC | GTGCCTGATA | 480
| TGGCGAAGGC | ACACCAAATT | CCTACACATC | CATCAGCCCC | CCCGAGGCGT | CTAATAATCT | 540
| TGCACACACA | TTGTCCCTGG | ATCCCTTCTT | TACTCCAGCC | TGTATG | | 586

FIG. 1b

PROMOTER REGION OF THE GENE FIM3

```
TAATGGCCTC CGGTAACGGA GGCCATTTTC ATTGGGCGAA GCCGCCCGCC GATCTGGGGC    60
GATTACCGGC AAATTCCCAC ACAACCATCA GCCCCCCCCC CGGACCTGAT ATTCTGATGC   120
CGACGCCAAG CACATGACGG CACCCCTCAG TATCAGAATC ACCATG                  166
```

FIG. 1c

```
fim 2  TGT TTCCCACA TCGGA ATCAG CCCCCCCCCCCCCCCCTAAGACCTAAGATCGTGGCTCCAT
fim X  AAA TTCCTACA  CATCC ATCAG CCCCCCCGAGGCGTCTAATAATCTTGCACACACAT
fim 3  AAA TTCCCACA  CAACC ATCAG CCCCCCCCCCGGACCTGATATTCTGATGCCGACGCCAAGCACAT
```

"pilinic box"        "box Cs"

1 2 3 4 5 6 7 8 9

1 2

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 429 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
CTGCAGGCCT  ACCCGGACAG  CACGCTCAAG  GGTCGCGCCA  ACCTGCTGGT  CATGCCCAAC         60
CTCGATACCG  GCAACATCAC  CTACAACATG  CTGAAGATGA  CCGGCAGCAA  CGGGATTCGA        120
TGGGCCCGAT  CCTGCTGGGT  TCGGCCCGCC  CGGTGCACAT  CCTGACCACC  AGCGCCACCG        180
TGCGCCGCAT  CGTCAACATG  ACGGCATTGG  CATGGTGGAC  GCGCAGCAGG  AAGCCGCCGA        240
AGGCTGACGC  TGATGCGCCG  GCCCGGCGCC  GCCATGGCGC  CGGGCCCTGC  ATGCACGGGT        300
CCAGTCCCGA  TAAAAGCCGC  ATGCAAAAGG  ACTGTTTCCC  ACATCGGAAT  CAGCCCCCCC        360
CCCCCCCCCT  AAGACCTAAG  ATCGTGGCTC  CATAACTCTT  CTGGCGCCAA  GACGCCCGTG        420
TTACCCATG                                                                    429
```

( 2 ) INFORMATION FOR SEQ ID NO:2:

( i ) SEQUENCE CHARACTERISTICS:
        ( A ) LENGTH: 586 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
GCGGCAGACG  CTGGCGGCGC  TGCTGGGCGA  AGTGCTCAAC  CTGCTCGGGC  GCACAGGCCT         60
TCGGGCTGCG  GTGCGGGCGA  GAACTGCGGT  CAAGCAGGCC  GTCCAGACCT  TCGCTTCGGA        120
AGCGGGCAAG  CCACTTGTAA  CCGGTGCGCA  GGCTGCACCC  CTGCCGCCTG  GCTGGCCTGG        180
CCTCATCGTC  CAGTTCTGTT  GCATCACCCT  GTTAACAAGA  AGGGCTCGAC  CTAGGCGGGT        240
CAATCGCGCA  TGCTTATGGT  TGTTCATCCA  GTGTCCTGCC  CTGAGTTGCG  ATGGCGTGGT        300
AACCACAGCA  TCCCAGGTCC  GGCCTGGATG  AACAACCTAT  TGAGACATCA  CACCTAGCGG        360
GGCGAATGCG  CGGATATCGA  GGCAGCTTGG  GCCAAATCCC  ATAAGCTGAC  GAACCCGCCC        420
CTCGATGGCA  GCCCAAACCC  TTACAACATA  AGTGGTTCCC  GCCGTCGTCC  GTGCCTGATA        480
TGGCGAAGGC  ACACCAAATT  CCTACACATC  CATCAGCCCC  CCCGAGGCGT  CTAATAATCT        540
```

TGCACACACA TTGTCCCTGG ATCCCTTCTT TACTCCAGCC TGTATG                          586

( 2 ) INFORMATION FOR SEQ ID NO:3:

( i ) SEQUENCE CHARACTERISTICS:
       ( A ) LENGTH: 166 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:3:

TAATGGCCTC CGGTAACGGA GGCCATTTTC ATTGCGCGAA GCCGCCCGCC GATCTGGCGC          60

GATTACCGGC AAATTCCCAC ACAACCATCA GCCCCCCCCC CGGACCTGAT ATTCTGATGC          120

CGACGCCAAG CACATGACGG CACCCCTCAG TATCAGAATC ACCATG                         166

( 2 ) INFORMATION FOR SEQ ID NO:4:

( i ) SEQUENCE CHARACTERISTICS:
       ( A ) LENGTH: 61 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:4:

TGTTTCCCAC ATCGGAATCA GCCCCCCCCC CCCCCCCTAA GACCTAAGAT CGTGGCTCCA          60

T                                                                          61

( 2 ) INFORMATION FOR SEQ ID NO:5:

( i ) SEQUENCE CHARACTERISTICS:
       ( A ) LENGTH: 56 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:5:

AAATTCCTAC ACATCCATCA GCCCCCCCGA GGCGTCTAAT AATCTTGCAC ACACAT              56

( 2 ) INFORMATION FOR SEQ ID NO:6:

( i ) SEQUENCE CHARACTERISTICS:
       ( A ) LENGTH: 65 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:6:

AAATTCCCAC ACAACCATCA GCCCCCCCCC CGGACCTGAT ATTCTGATGC CGACGCCAAG          60

CACAT                                                                      65

( 2 ) INFORMATION FOR SEQ ID NO:7:

( i ) SEQUENCE CHARACTERISTICS:
       ( A ) LENGTH: 16 base pairs
       ( B ) TYPE: nucleic acid
       ( C ) STRANDEDNESS: single
       ( D ) TOPOLOGY: linear ( i i ) MOLECULE TYPE: DNA ( x i ) SEQUENCE DESCRIPTION: SEQ ID NO:7:

CCTTCAGCTT GATGAT                                                                           16

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GTGATGACGA TGGTG                                                                            15

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GACCTGATAT TCTGATGCCG ACGCCAAGCA CATGA                                                      35

( 2 ) INFORMATION FOR SEQ ID NO:10:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

AGCTTCATGT GCTTGGCGTC GGCATCAGAA TATCAG                                                     36

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TAAGACCTAA GATCGTGGCT CCATA                                                                 25

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

AGCTTATGGA GCCACGATCT TAGGTC                                                                26

PROMOTER OF THE GENE WHICH CODES FOR THE PILINIC SUBUNIT FIM3 OF *BORDETELLA PERTUSSIS* AND ITS USE FOR THE EXPRESSION IN BORDETELLA OF THE GENES WHICH CODE FOR A PROTEIN OF INTEREST

This is a continuation of patent application Ser. No. 07/607,966, filed Oct. 31, 1990, now abandoned.

DESCRIPTION

The present invention relates in general to the isolation and characterisation of the promoter regions of the genes which code for the pilinic subunits fim2, fim3 and fimx of *Bordetella pertussis*, vectors containing the regions, microorganisms transformed by the vectors, and the use thereof for the expression of genes which code for a protein of interest.

In particular, the present invention relates to the use of the promoter regions or nucleotide fragments thereof for the regulated or non-regulated expression of genes which code for a protein of interest in a strain of Bordetella and the use of that strain for the development of an effective anti-pertussis vaccine.

BACKGROUND OF THE INVENTION

*Bordetella pertussis* (*B. pertussis*) is the etiological agent of pertussis, a disease of the respiratory tract which is transmitted from a sick person to a susceptible healthy individual during the virulent stage.

Pertussis, which is characterised by convulsive coughing fits and serious respiratory symptomology, strikes individuals of all ages and, in the first years of life, may cause death in 0.5% of cases.

The incidence of the infection can be controlled effectively by immunisation with a suitable vaccine.

Currently, a cellular anti-pertussis vaccine is used, that is, a vaccine constituted by entire virulent *B.pertussis* cells treated with merthiolate and killed at 56° C. Whilst it confers protective immunity, this vaccine may, however, induces undesirable side effects ranging from simple wheals, erythema and fever to convulsions and brain damage. For these reasons, the use of this vaccine has been drastically reduced in recent years resulting in a new explosion of pertussis cases.

As a result, there is a need to develop an anti-pertussis vaccine which does not have the disadvantages described above.

It is known that, during the virulent stage (Stage I), *B.pertussis* produces a series of toxic components (virulence factors) which are necessary in order for the infection to arise and persist, and some of which seem to be immunogens particularly suitable for the development of an acellular anti-pertussis vaccine.

Thus, for example, the pili or fimbriae, which are proteins present on the surface of the bacterium, and are constituted by polymerised (pilinic) subunits with molecular weights of from 21,000 to 24,000 Daltons, are involved in the specific adhesion of the bacteria to the cilia of the epithelial cells of the upper respiratory tract.

This is an essential stage in the pathogenisis of pertussis since it enables the microorganism to elude the host's defensive system. A vaccine against this stage would therefore be desirable.

Ashworth et al (1982) (*Infect. Immun.*, 37, 1278-1281) first suggested that the pili of *B.pertussis* were sertotype-specific agglutinogens, that is surface antigens which stimulate the production of antibodies which agglutinate bacterial cells of the same serotype.

Currently, antigenically different pilinic proteins belonging to serotypes 1, 2, 3, 4, 5, 6 and x have been identified.

The use of purified pili for the preparation of a vaccine must, however, take account of the antigenic variation observed in strains of *B.pertussis*.

In fact it has been found that, whilst some of these antigens are present in all the strains of *B.pertussis*, those associated with the fimbriae 2, 3, 4, 5 and 6 are present in different combinations not only in different strains, but also in different isolated samples of the same strain.

An ideal vaccine, that is a vaccine which can confer protective immunity against any infective strain of *B.pertussis*, should therefore contain all the serotypically different antigens.

The preparation of such a vaccine presents many problems resulting, on the one hand, from the fact that it is difficult to isolate and purify these antigens and, on the other hand, from their limited availability.

For these reasons, it would seem desirable to prepare a strain of Bordetella which can produce all the pilinic subunits with high yields.

The structural genes which code for the subunits fim2 and fimx of *B.pertussis* have recently been cloned and sequenced (Livey, J. et al., (1987), Mol. Microbiol., 1 (2), 203-209; Pedroni, P. et al., (1988), Mol. Microbiol., 2, 539-543).

Up to now, however, nothing has been known about the regulation of the expression of these genes and, in particular, the nucleotide sequences of their promoters were not known.

SUMMARY OF THE INVENTION

A subject of the present invention is therefore the isolation and characterisation of the promoter regions of the fim2, fim3 and fimx genes of *Bordetella pertussis*.

Another subject of the present invention is the use of the promoter regions or fragments thereof for the regulated and non-regulated expression of genes which code for a protein of interest in Bordetella.

A further subject of the present invention is a cloning vector for expression in host organisms selected from the Bordetella group containing the promoter region or a fragment thereof.

A further subject of the present invention is a strain of Bordetella transformed by the vector.

Another subject of the present invention is an anti-pertussis vaccine including a strain of Bordetella which contains at least one of the said promoter regions and can express a protein of interest, in a regulated or non-regulated manner.

Further subjects of the present invention will become clear from a reading of the following description and experimental examples.

BRIEF DESCRIPTION OF THE PREFERRED EMBODIMENTS

According to the present invention, the promoter regions of the fim2, fim3 and fimx genes were isolated by known techniques, from positive clones obtained from a gene library in cosmids, starting from the *B.pertussis* SA1 strain (SCLAVO). In practice, the gene library was prepared by the partial or complete digestion of the chromosomal DNA extracted from the bacterium with suitable restriction enzymes, the cloning of the digestion fragments in cosmids, the transformation of a host organism by the cosmids, and finally the selection of the positive clones, that is those containing the cosmid including a fragment of chromosomal DNA which can give a hybridization reaction with specific probes.

Three clones were isolated as described above and contained, respectively, a 4400-base-pair (bp) fragment containing the structural gene and the promoter region of fim2, a 2900-bp fragment containing the structural gene and the promoter region of fim3 and a fragment of approximately 3300 bp, containing the structural gene and the promoter region of fimx.

The promoter regions were then isolated from the fragments.

In practice, a BamHI-HindIII fragment of about 400 bp containing the promoter region of the fim2 gene was isolated from the 4400-bp fragment and cloned in a cloning vector to produce the hybrid plasmid pSM 351 (Example 8).

In parallel, an HaeII-BamHI fragment of approximately 550 bp containing the promoter region of the fimx gene was isolated from the fragment of approximately 3300 bp and, after its HaeII end had been blunted, was cloned in a vector to produce the plasmid pSM 346 (Example 5).

A PstI-AvaII fragment of approximately 1300 bp containing the promoter region of fim3 was also isolated from the fragment of approximately 2900 bp and then cloned in a vector to produce the plasmid pSM 349 (Example 6).

According to the present invention, these promoter regions were sequenced by the technique of Sanger et al., (1977), (*Proc. Nat'l. Acad. Sci.* 74:5463) with the use of the successive primers strategy described by Strauss et al., (1986), (*Anal. Biochem.*, 154:553).

The sequencing reactions were carried out by the normal Boehringer method on the plasmids, which had been denatured with the use of a "pUC sequencing" kit.

The results obtained showed the presence of highly homologous regions upstream of the presumed transcription-start sites in the three promoters.

In particular, these regions could be identified as follows:
1) a series of Cs, known as the "Cs box", situated around the nucleotide in position $-35$;
2) a second similar region, known as the "pilinic box", which was situated immediately upstream of the "Cs box" and showed no similarity to other sequences of *B.pertussis* genes.

It is known that the genes which code for the virulence factors are all situated on the Bordetella chromosome and are positively regulated in a coordinated manner by a single vir locus whose products interact with the sequences upstream of these genes.

In fact, if the vir locus is made inactive by mutagenesis with a transposon, the ability of the bacteria to produce the virulence factors is lost (Weiss et al., (1983), *Infect. Immun.*, 42, 33–41).

A similar loss of the virulence mediated by the vir locus is observed in *B.pertussis* under the following circumstances:
  a change from the virulent stage I to the non-virulent stage III, and
  modulation by a change in the composition of the culture medium or in the temperature.

Whilst the change in stage causes a stable loss of virulence which is only rarely reversible, modulation by external factors gives rise to a reversible phenotypical expression which can be induced or repressed by the growth of the bacteria at low or high temperature, or in the presense or in the absence of chemical substances such as magnesium sulphate or nicotinic acid.

In order to check whether the isolated promoter regions and, in particular, the sequences identified corresponded to elements which regulate the transcription mediated by the vir locus or modulated by a change in the culture conditions, the nucleotide fragments including the promoter regions of the fim2, fim3 and fimx genes were isolated from the plasmids pSM 351, pSM 349 and pSM 346 respectively, ligated to the 1630-bp HindIII-XbaI fragment containing the CAT gene without its own promoter and then cloned in a wide-spectrum plasmid such as, for example, pLA FR2.

The recombinant plasmids, which showed the correct insertion of the promoter region and the CAT gene were then introduced into *B.bronchiseptica* (Bb) strains 7865 and 7866 by conjugation by the technique described by Gross et al (*Proc. Nat'l. Acad. Sci.*, USA 85, 3913–3917, 1988). The Bb strain 7866 is a vir$^-$ strain produced by spontaneous mutation from the Bb strain 7865 (vir$^+$). Both strains are publicly available.

The extracts of the conjugants were then examined to determine their chloramphenicol acetyl transferase activities, as described by Gross et al (PNAS, USA 85, 3913–3917, 1988). The results obtained (FIG. 9) indicated that:
  the vir$^+$ strains containing the promoters of the genes which code for the pilinic subunits fim2, fim3 and fimx were able to direct the expression of the heterologous CAT gene; and
  the promoters of the three pilinic genes had different strengths. In particular, the promoter of the fim2 gene was the strongest, whilst those of the fimx and fim3 genes were 150 times and 3 times weaker than that of fim2 respectively.

Moreover, the absence of CAT activity in the conjugants derived from the vir$^-$ Bb strain containing the promoter regions of the fim2 and fimx genes confirmed that the sequences identified as the "Cs box" and the "pilinic box" represent sequences which control the regulation of the transcription of the genes and whose activation depends on the presence of functioning components of the vir system.

The presence of CAT activity in the vir$^-$ strain containing the promoter region of the fim3 gene, however, indicated that the sequences identified above are not regulated by the vir locus and that the fim3 promoter behaves as a constitutive promoter.

This term means a promotor which is active regardless of the presence of effectors, that is proteins or chemical or physical agents which can regulate the expression of a gene.

In order to check the role of the "Cs box" and "pilinic box" sequences of the fim2 and fimx promoters, three mutants of the fim2 promoter region were constructed.

Either the Cs box (pR2 $\Delta$1), or the pilinic box (pR2 $\Delta$2), or both boxes (pR2 $\Delta$1-2) were deleted from these promoters. Analysis of the acetyl transferase activities of the vir$^+$ *B. bronchiseptica* strains containing the CAT gene whose promoter had been replaced by each of the mutated promoters described above showed that both sequences were essential for promoting transcription. Moreover, according to the present invention, the modulation was verified by the cultivation of vir$^+$ *B.bronchiseptica* cells transformed by the plasmid pR 2 and by each of the plasmids containing the mutated promoter, in the presence of and without MgSO$_4$. The results (FIG. 11) show that the fim2 gene promoter is subject to modulation and completely loses its activity in the presence of 50 mM MgSO$_4$. The same promoter modified by the deletion of one or both boxes was no longer able to vary its activity under non-permissive conditions.

The promotor regions of the fim2 and fimx genes according to the present invention, or fragments thereof containing the transcription-regulation elements, therefore seem to be particularly suitable for the construction of vectors for the regulated expression in Bordetella of a structural gene which codes for a protein of interest, in which the gene is placed in the correct reading phase under the control of the promoters.

Vectors suitable for the purposes of the present invention may be plasmids selected from those which replicate or integrate into the genome in Bordetella selected from those of the prior art.

Bordetella strains may be selected from the group of B.pertussis, B.bronchiseptica and B.parapertussis.

The heterologous gene may be any gene which codes for a protein of interest.

Preferably, the gene codes for an immunogenic protein produced by virulent Bordetella pertussis, for example pilinic subunits, pertussis toxin or subunits thereof, adenylate cyclase, haemagglutinin filamentosa or the protein 69K.

According to one embodiment of the present invention, the constitutive promoter of the fim3 gene or a fragment thereof may be used for the non-regulated expression of a protein of interest in vir$^-$ strains of Bordetella. This seems to be particularly advantageous since it enables operation with non-pathogenic strains.

The vir$^+$ or vir$^-$ strains of Bordetella thus obtained are very useful for the preparation of an anti-pertussis vaccine.

Brief description of the drawings

FIG. 1 (parts a,b, and c) shows the nucleotide sequences of the promoter regions of the genes which code for the pilinic subunits fim2 (SEQ. ID. No. 1), fimx (SEQ. ID. No. 2) and fim3 (SEQ. ID. No. 3), FIG. 9 shows the results of the CAT test carried out on cell extracts of vir$^+$ and vir$^-$ strains of B.bronchiseptica transformed by the plasmids pR2, pR3P, pRx, and positive and negative control plasmids in which:

1 and 2 relate to the negative control in vir$^+$ and vir$^-$ strains, 3 relates to the positive control containing the pertussis toxin gene in a vir$^+$ strain, 4 and 5 relate respectively to the vir$^+$ and vir$^-$ strains transformed by pR2, 6 and 7 relate respectively to the vir$^+$ and vir$^-$ strains transformed by pR3P, 8 and 9 relate respectively to the vir$^+$ and vir$^-$ strains transformed by pRx.

Figures 2, 3:
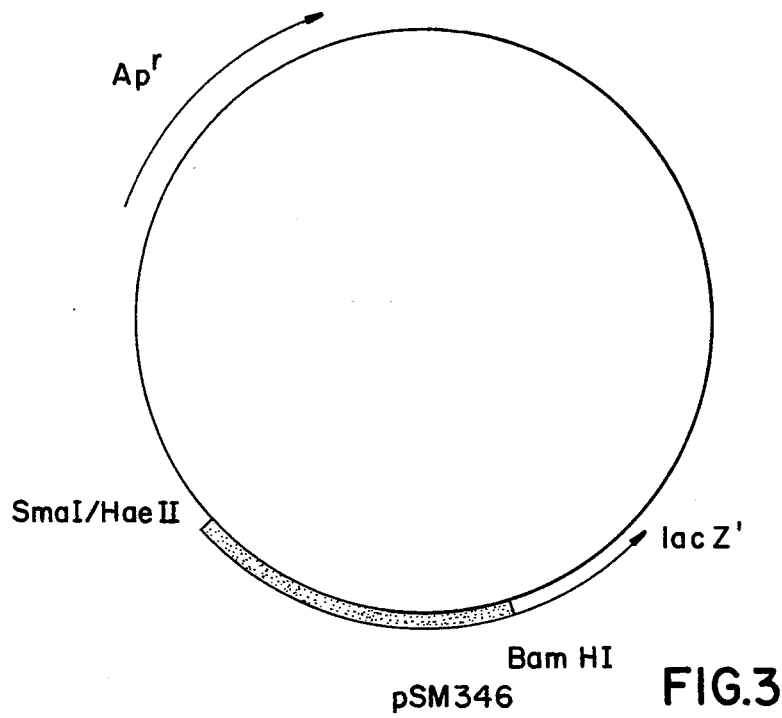
FIG. 2 shows the nucleotide sequences of the "Cs boxes" and the "pilinic boxes" included in the promoter regions of the genes which code for the pilinic subunits fim2, fimx and fim3 (SEQ. ID. No. 4, No. 5, No. 6) respectively.
FIG. 3 shows the restriction map of the plasmid pSM 346.

The vectors containing the promoter regions of fim2, fim3 and fimx were deposited as E.coli 71.18 (pSM 351), E.coli JM 101 (PSM 349) and E.coli 71.18 (pSM 346) respectively at the American Type Culture Collection, as ATCC 68069, ATCC 68105 and ATCC 68068.

The experimental examples which follow are illustrative of the invention and are not limiting.

Example 1

Extraction of the chromosomal DNA from B.pertussis SA1

100 ml of fermentation medium having the following composition:

| | |
|---|---|
| Beta casamino acids (Difco) | 14 g |
| KCl | 0.2 g |
| MgCl$_2$.6H$_2$O | 0.1 g |
| K$_2$PO$_4$ | 0.5 g |
| nicotinic acid | 0.02 g |
| glutathione | 0.01 g |
| starch | 1.00 g |
| H$_2$O | 1 l |
| pH 6.8 | | was sterilised beforehand at 120° C. for 15 minutes, and was inoculated with B.pertussis strain SA1 and kept under agitation (200 revolutions per minute, rpm) at 37° C. for 3 days.

At the end of this period, the cells were separated from the supernatant liquid by centrifuging in a Sorvall RC-5B Model SS34 rotor at 4° C. at 5000 rpm for 10 minutes and then washed (2×120 ml) with a solution containing 100 mM NaCl, 50 mM Tris-HCl, pH 7.5.

The resulting suspension was centrifuged again as described above and the cells were recovered and resuspended in 10 ml of buffer solution (100 mM EDTA, 50 mM NaCl, 2.5% sucrose, pH 6.9) containing 1 mg/ml of lysozyme (SIGMA).

The suspension was kept under mild agitation at 37° C. for 30 minutes and SDS (sodium dodecyl sulphate) was then added to give a final concentration of 1% and kept at 60° C. for 30 minutes.

1 mg/ml of K proteinase, previously incubated at 37° C. for 30 minutes in 1×SSC (1×SSC=0.15 M NaCl, 15 mM sodium citrate) was then added to the solution and the resulting mixture was reacted at 37° C. for 2 hours.

After the addition of NaCl to give a final concentration of 1M, the mixture was kept in ice for 30 minutes and then centrifuged. The DNA contained in the supernatant liquid was precipitated with 2-3 volumes of cold ethanol (−20° C.), collected with a glass rod, and resuspended in 10 ml of 0.1×SSC. The suspension was kept under mild agitation at ambient temperature (20°-25° C.) for one night and, after the addition of RNAse (10 gamma/ml), was kept at 37° C. for 30 minutes.

The saline concentration of the solution was then brought to 1×SSC, the solution was extracted with phenol (1 volume) and the DNA was precipitated by the addition of isopropanol dropwise to the solution which was kept under mild agitation and at ambient temperature. The DNA was then recovered by centrifuging and resuspended in 1 ml of 0.01×SSC.

The quantity of chromosomal DNA, evaluated by a spectrophotometric reading at OD 260 with the use of a Perkin Elmer spectrophotometer Mod. 515, was 0.645 mg/ml.

Example 2

Isolation of the Promoter Regions of the Fim2 and Fim3 Genes

In order to isolate and characterise the sequences of the promoter regions of the fim2 and fim3 genes, a genome bank of B.pertussis SA1 was constructed with the use of the cosmid pHC 79 (Honn, B. and Collins, J., (1980), Gene 11, 2.91–298).

500 μg of the chromosomal DNA of B.pertussis SA1 extracted as described in Example 1, were partially digested with 5 units of Sau 3A (BRL). The digestion was carried out in a buffer mixture at 37° C. for 15 minutes.

The DNA thus digested was precipitated by the addition to the solution of an equal volume of ethanol and, after separation, the DNA was resuspended in 0.5 ml of 10 mM Tris-HCl, pH 7.5, 1 mM EDTA buffer. The solution was loaded onto a 10% to 40% sucrose gradient dissolved in 35 ml of 1 mM NaCl, 10 mM Tris-HCl pH 7.5, 1 mM EDTA buffer. The gradient was then centrifuged at 26,000 rpm for 16 hours in a Beckman SW28 rotor and fractions, each of 1 ml, were collected. The molecular weight of the DNA obtained in each fraction was determined by electrophoresis on agarose. (Maniatis et al. "Molecular Cloning: a practical laboratory manual", Cold Spring Harbor, N.Y., 1982). The fractions containing DNA fragments of 35–45 kb were then dialysed, the DNA was precipitated with ethanol as described above and, after separation by centrifuging, was resuspended in 10 mM Tris-HCl, pH 7.5, 1 mM EDTA buffer at a concentration of 1 μg/ml. The chromosomal DNA fragments were then cloned in the cosmid pHC 79.

In practice, 10 μg of the cosmid were digested with 40 units of the restriction enzyme BamHI (BRL) at 37° C. for 1 hour in 200 μl of buffer mixture.

2 μg of chromosomal DNA were ligated with 0.5 μg of cosmid DNA in 10 μl of ligation mixture in the presence of 1 unit of T4 DNA ligase at 14° C. for one night.

At the end of this period, 2.5 μl of the ligation mixture were used in vitro with Stratagene's Packagene Kit. The recombinant cosmids thus obtained were used to infect the E.coli strain JM 109 (BRL) and the transformants were selected on LB agar medium (DIFCO). 15,000 positive colonies were selected.

About 1500 of these colonies were analysed with the use of the following probes:

Probe 3: CCTTCAGCTTGATGAT (SEQ. ID. No. 7)

Probe 4: GTGATGACGATGGTG (SEQ. ID. No. 8)

The oligonucleotides were synthesised with the use of a Beckman SYSTEM ONE PLUS automatic system and then marked at their 5'OH ends with $10^5$ μCi of gamma ($p^{32}$) ATP as follows:

200 ng of each oligonucleotide were suspended in 30 μl of an aqueous solution constituted by 3 μl of kinase buffer (Boehringer), 21 μl ATP, 10 units per ml T4 polynucleotide kinase (1 μl).

The mixture was kept at 37° C. for 45 minutes and then at 65° C. for 10 minutes to de-activate the enzyme.

The marked probes were purified in Sephadex G-50 columns in pH 8.00 TE buffer to eliminate the marker which had not been incorporated. 13 fractions each of 150 μl were collected. 2 μl of each fraction were placed in 4 ml of scintillating liquid and measured with a scintillator.

The positive colonies of the bank in cosmids were transferred onto nitrocellulose filters (Schleicher & Schull 0.45 μm) and after lysis with NaOH, their DNA was immobilised by the Southern blot technique (Maniatis et al, 1982).

The filters were hybridised, in parallel, with the pair of probes described above. The prehybridisation treatment was carried out at 65° C. for 6 hours, whilst the hybridisation treatment was effected at:

41° C. for one night with the probe 3; and

45° C. for one night with the probe 4.

The filters were then washed at 25° C. with 0.1% sodium dodecyl sulphate (SDS), 6×SSC for 1 hour and placed in contact with Kodak X-Omat AR radiographic plates. 5 clones which hybridised with both the probes were isolated as described above.

One of the cosmids extracted from the clones contained the 4400-bp PstI fragment including both the fim2 promoter and its structural gene, whilst another cosmid contained the 2900-bp PstI fragment including the fm3 promoter and structural gene.

These fragments were isolated by the digestion of the cosmid DNA with PstI and were introduced into the plasmid pUC 18, which had previously been digested with PstI to produce the hybrid plasmids pSM 352 and pSM 348.

Example 3

Isolation of the Promoter Region of Fimx

5 μg of the chromosomal DNA prepared as in Example 1 were digested completely with 80 units of EcoRI (BRL) under the conditions suggested by the suppliers. The digestion mixture was then loaded onto 0.8% agarose gel and run at 20 volts for one night. At the end of this period, the region between 3.0 and 4.0 kb was electroeluted and purified by extraction with phenol. After the precipitation of the DNA with cold ethanol and separation by centrifuging, 190 ng of DNA were ligated with 50 ng of pUC 13 plasmid DNA digested with EcoRI. The reaction was carried out by the suspension of the reagents in 25 μl of ligation buffer in the presence of 1 unit of T4 DNA ligase at 12° C. for one night.

The mixture was then used to transform competent E.coli JM 101 cells (BRL). The transformants were selected on LB agar medium (DIFCO) to which 50 μg/ml of ampicillin, 125 μg/ml of IPTG and 40 μg/ml of X-Gal (PROMEGA) had been added. The positive clones obtained (600) were transferred onto nitrocellulose filters (Schleicher & Schnell) and the DNA extracted from the clones was hybridised with a probe whose nucleotide sequence corresponded to the 790-bp BamHI-PstI region of the fimx structural gene and which was marked by Boehringer's "random primer labelling" method.

The prehybridisation reaction was carried out at 68° C. for 6 hours and the hybridisation reaction at 68° C. for one night, with the use of the Southern transfer technique described by Maniatis et al (1982). The filters were washed by the plate-washing technique described by Maniatis et al (1982).

15 of the clones examined gave positive signals and all the cosmids extracted from the clones contained EcoRI-EcoRI bands of approximately 3300 bp containing both the fimx structural gene and its promoter region.

This 3300-bp fragment was inserted in the pUC 12 plasmid, which had been digested beforehand with EcoRI, to give the plasmid pSM 281.

Example 4

Sequencing of the promoter regions of the fim2, fim3 and Fimx Genes

The promoter regions of the fim2, fim3 and fimx genes contained in the plasmids pSM 352, pSM 348 and pSM 281 respectively were partially sequenced, starting from the ATG translation-start site, by the method of Sanger et al., (1977), (PNAS, 74, 5463) with the use of the successive primers strategy described by Strauss et al., (Anal. Biochem., 154, 553, (1986)). The oligonucleotides used as primers were synthesised by means of an automatic System 1 Plus DNA synthesiser system (Beckman). The sequencing reactions were carried out according to the normal Boehringer method on the denatured plasmids with the use of a "pUC sequencing" kit with alpha ($p^{32}$) dATP as the tracer. The equipment used for the electrophoretic separation was a macrophor sequencing system (LKB).

The partial nucleotide sequences of the promoter regions of the three genes were constituted by 430 bp (SEQ. ID. No: 1), 166 bp (SEQ ID NO: 3) and 586 bp (SEQ ID NO:2), respectively, and are given in FIG. 1.

Analysis of the sequences upstream of the presumed transcription-start sites showed highly homologous regions in the three promoters which could be identified as follows:

1) a series of Cs, the "Cs box", situated around the nucleotide in position −35;

2) a second homologous region, the pilinic box, which was situated immediately upstream thereof and showed no similarity to other sequences of the B.pertussis genes.

The sequences of the boxes are given in FIG. 2.

Example 5

Construction of the Plasmid pSM 346

The plasmid pSM 281 was digested with HaeII add BamHI restriction enzymes (BRL) according to the supplier's suggestions.

The HaeII-BamHI fragment of approximately 550 bp containing only the fimx promoter region was isolated from the digestion mixture, blunted at the HaeII end and then subcloned in the pUC 12 plasmid digested with SmaI and BamHI. The resulting plasmid was indicated pSM 346 (FIG. 3 ).

Example 6

Construction of the Plasmid pSM 349

The 1300-bp PstI-AVAII fragment containing the fim3 promoter was isolated from pSM 348. Since the restriction enzyme AvaII cuts 36 bases upstream of the transcription-start site (CAT), in order to recreate this sequence, an AvaII-HindIII oligonucleotide was synthesised, which had the following sequence:

```
        AvaII
GACCTGATATTCTGATGCCGACGCCAAGCACATGA (SEQ. ID. No. 9)
   GACTATAAGACTACGGCTGCGGTTCGTGTACTTCGA (the 3' to 5' sequence of SEQ. ID. No. 10)
                                   HindIII
``` and in which the HindIII site was inserted immediately after the mRNA transcription-start site.

1.5 µg of the 1300-bp PstI-AvaII fragment and 3.75 µg of the AvaII-HindIII synthetic oligonucleotide, which had been phosphorylated beforehand with polynucleotide kinase enzyme, were ligated to each other in 75 µl of ligation mixture. The ligation product thus obtained (1336 bp) was purified on 0.8% agarose gel, recovered and precipitated at −20° C. for one night. The product (75 ng) was then ligated to 50 ng of the vector pUC 13 digested with 2 units of PstI and HindIII in 20 µl of ligation mixture containing 1 unit of T4 DNA ligase at 14° C. for one night.

The ligation mixture was used to transform competent E.coli JM 101 cells and the transformants were selected on LB medium to which ampicillin, X-GAL and IPTG had been added.

Figure 4:
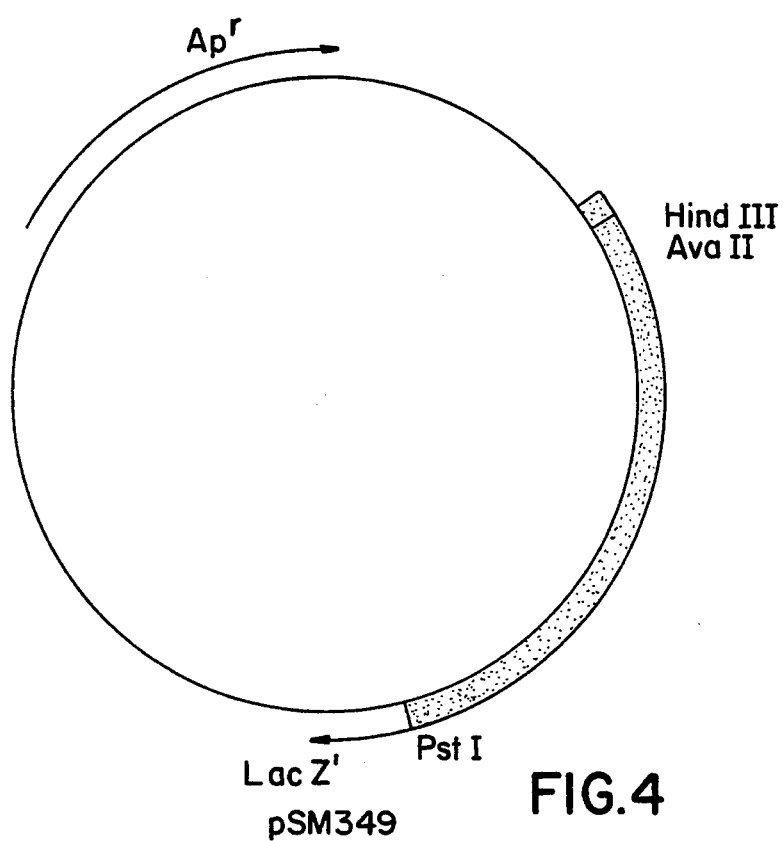
FIG. 4 shows the restriction map of the plasmid pSM 349.

The plasmid pSM 349 containing the 1336-bp PstI-HindIII insert was isolated from one of the positive clones (FIG. 4).

Example 7

Construction of the Plasmid RSM 350

The plasmid pSM 349 produced in Example 4 was digested with 5 units of HindIII which cuts at the site immediately following the transcription-start site and 5 units of HindII which cuts 370 bp upstream of the HindIII site.

The 370-bp DNA fragment isolated from the digestion mixture was then ligated with the plasmid pUC 13, which had previously been cut by HindIII and HindII.

The transformation of E.coli JM 101 cells by the ligation mixture enabled the plasmid pSM 350 containing the 370-bp fragment of the promotor region of fim3 to be isolated.

Example 8

Construction of the Plasmid pSM 351

The StuI fragment of approximately 700 bp constituted by the sequence of about 430 bp of the promoter region of fim2 and that of 280 bp of its structural gene was isolated from the plasmid pSM 352 and cloned in the plasmid pUC 12 (1 µg) which had been digested beforehand with 5 units of SmaI restriction enzyme (BRL).

The cloning was carried out with the use of 60 ng of the vector and 40 ng of the fragment in 20 µl of ligation mixture in the presence of 1 unit of T4 DNA ligase at 23° C. for one night. The ligation mixture was then used to transform E.coli JM 101 cells and the transformants were selected on LB medium to which X-gal (5-bromo-4-chloro-3-indoyl-β-D-galactoside), IPTG (isopropyl-β-D-thiogalactopyranoside) and ampicillin had been added.

A plasmid containing the fragment of about 700 bp was extracted from a positive clone. The promoter region of about 380 bp was then isolated from the plasmid by digestion with BamHI (BRL), whose restriction site is situated immediately before the SmaI site in the multiple cloning site (mcs) of the vector, and with DdeI which cuts 21 bp upstream of the transcription-start site.

In order to recreate the 21-bp sequence which extends from the transcription-start site (CAT) to the DdeI site and to position the HindIII site immediately after CAT, a DdeI-HindIII oligonucleotide was synthesised and had the following sequence:

TAAGACCTAAGATCGTGGCTCCATA (SEQ. ID. No. 11)
 CTGGATTCTAGCACCGAGGTATTCGA (the 3' to 5' sequence of SEQ ID. No. 12)
   HindIII The HindIII site is located immediately after the transcription-start site.

The BamHI-DdeI DNA fragment of about 380 bp (1.5 µg), and the DdeI-HindIII synthetic oligonucleotide. (3.75 µg) which had been phosphorylated beforehand with polynucleotide kinase enzyme (Boehringer) were ligated to each other in 75 µl of ligation mixture.

The reaction was carried out in the presence of 20 units of T4 DNA ligase at 14° C. for one night.

The ligation product thus obtained was purified on 0.8% agarose gel, recovered by the method described in Methods in Enzymology, 65, 526, 1980 and precipitated with ethanol at −20° C. for one night.

The purified product (22 ng) was then ligated to 50 ng of the vector pUC 12 digested with 1 unit of BamHI and HindIII in 25 µl of ligation mixture.

The reaction was carried out in the presence of 1 unit of T4 DNA ligase at 14° C. for one night.

The ligation mixture was then used to transform E.coli 71.18 cells and the transformants were selected on LB medium to which 50 µg/ml of ampicillin, X-GAL and IPTG had been added.

Figure 5:
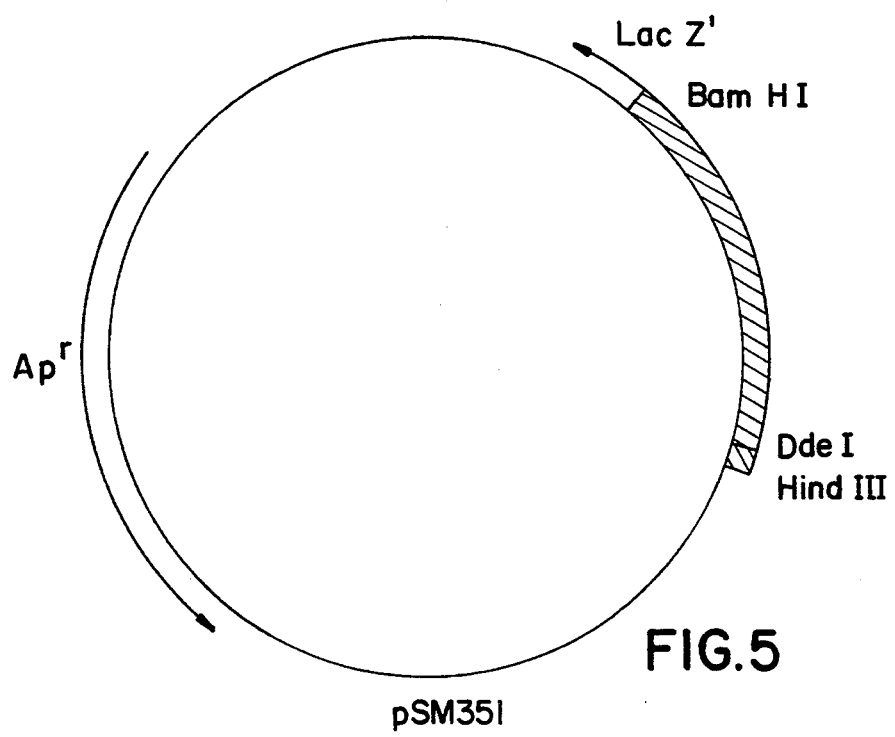
FIG. 5 shows the restriction map of the plasmid pSM 351.

The plasmid pSM 351 containing the fim2 promoter region of about 400 bp was isolated from one of the positive clones (FIG. 5).

Example 9

Construction of the Plasmid pR 2

The BamHI-HindIII fragment of about 400 bp of the promoter region of the fim2 gene (100 ng) obtained by enzymatic digestion from the clone pSM 351 was ligated with 100 µg of the HindIII-XbaI fragment of 1630 bp containing the CAT gene without its own promoter and with 200 ng of the plasmid pLA FR2 which had been digested with 10 units of BamHI and 10 of XbaI. The ligation reaction (30 µl) was carried out in the presence of 3 units of T4 DNA ligase at 14° C. for one night and used to transform competent E.coli 5K cells. The transformants were selected on LB agar medium to which 12.5 µg/ml of tetracycline had been added.

Figure 6:
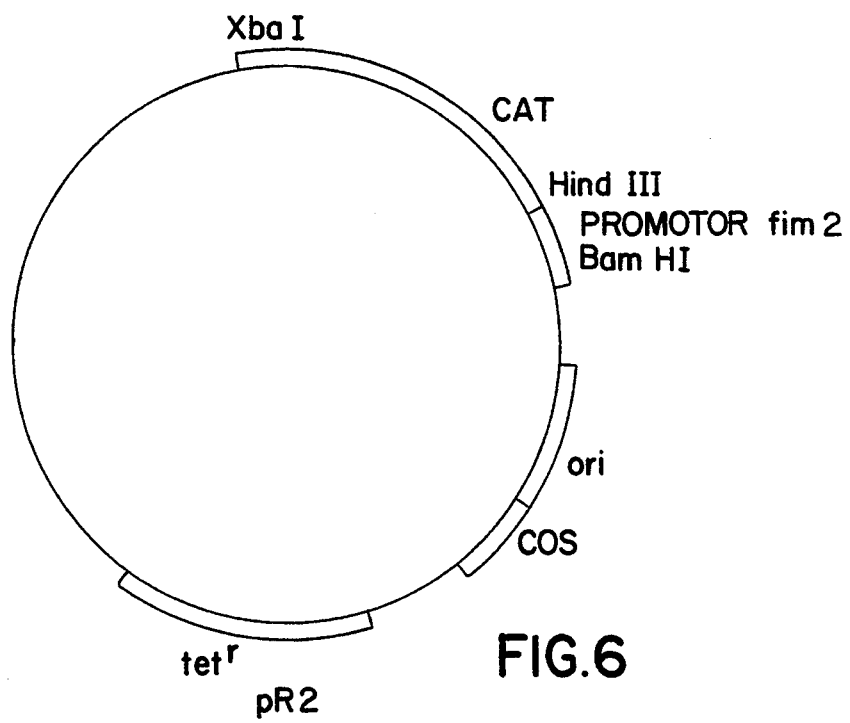
FIG. 6 shows the restriction map of the plasmid pR2.

The plasmid pR 2 which showed the correct insertion of the promoter region and of the CAT gene was isolated from one of the clones (FIG. 6).

Example 10

Construction of the Plasmid pRx.

The EcoRI-BamHI fragment of about 560 bp including the promoter of the fimx gene was isolated from the plasmid pSM 346 by digestion with the restriction enzymes EcoRI and BamHI.

Figure 7:
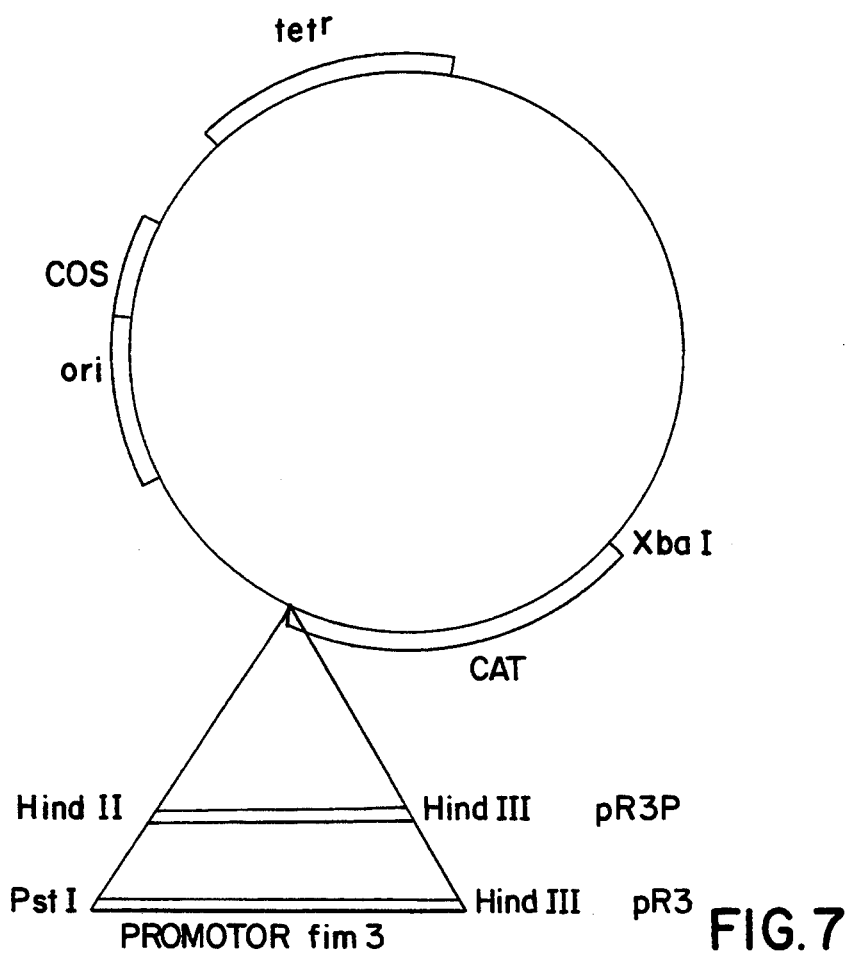
FIG. 7 shows the restriction map of the plasmids pR3, and pR3P.

110 µg of the fragment blunted at both ends and 100 ng of the HindIII-XbaI fragment containing the CAT gene without its promoter, blunted at the HindIII end were ligated with the plasmid pLA FR2 (200 ng) which had been digested beforehand with BamHI and XbaI and blunted at the BamHI end. The ligation reaction (30 µl) was carried out in the presence of 5 units of T4 DNA ligase at 23° C. for one night and used to transform E.coli 5K cells. The transformants were selected on LB agar medium to which 12.5 µg/ml of tetracycline had been added. The plasmid pRx was isolated from one of the positive clones and showed the correct insertion of the promoter region and of the CAT gene (FIG. 7).

Example 11

Construction of the plasmids pR3, pR3P.

A) Construction of pR3.

The PstI-HindIII fragment of 1336 bp containing the promoter region of the fim3 gene (200 ng) obtained from the plasmid pSM 349 was ligated with 100 ng of the 1630-bp HindIII-XbaI I fragment containing the CAT gene without its own promoter and with 200 ng of the plasmid pLA FR2 which had been digested with 10 units of PstI and 10 of XbaI. The reaction was carried out in 30 µl of ligation mixture in the presence of 3 units of T4 DNA ligase at 14° C. for one night and used to transform competent E.coli 5K cells.

The transformats were selected on LB agar to which tetracycline (12.5 µg/ml) had been added.

Figure 8:
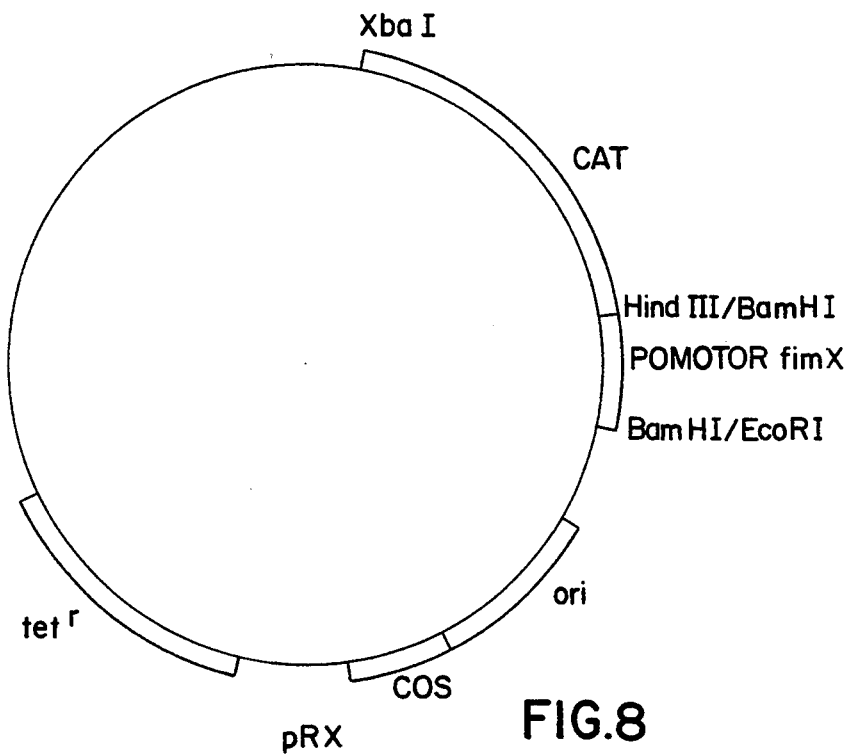
FIG. 8 shows the restriction map of the plasmid pRx.

The plasmid pR3 was extracted from one of the positive clones and had the expected characteristics (FIG. 8).

B) Construction of pR 3P.

The BamHI-HindIII fragment of 370 bp containing a portion of the promoter region of fim3 (200 ng) was isolated from the plasmid pSM 350 by enzymatic digestion with BamHI and HindIII.

The fragment was then ligated with the 1630-bp HindIII-XbaI fragment (100 ng) and with the plasmid pLA FR2 digested with BamHI and XbaI. The plasmid pR 3P was isolated by the transformation of E.coli cells and the subsequent selection of the positive clones (FIG. 8).

Example 12

Construction of the Negative Control pLA FR2-CAT

The negative control was constructed by the ligation of 45 ng of the 1630-bp HindIII-XbaI fragment blunted at the HindIII end with 200 ng of the vector pLA FR2 which had been digested with BamHI and XbaI and blunted at the BamHI end. The ligation reaction (17 µl) was carried out in the presence of 4 units of T4 DNA ligase at 23° C. for one night and used to transform competent E.coli 5K cells.

The transformants were selected on LB agar medium to which tetracycline had been added. The plasmid pLA FR2-CAT was extracted from one of the positive clones.

Example 13

Transformation of vir+ and vir− strains of B.bronchiseptica by the plasmids pR2, pRx and pR3 and pLA FR2-CAT.

A) Conjugation

In order to transfer the plasmids into *B. bronchiseptica* 7865 (vir+) and 7866 (vir−) a preliminary transfer into the mobilising strain *E.coli* SM10 was necessary. This strain contains the genes necessary for transferring the conjugative plasmid pLA FR2 into a receiving strain, in this case *B.bronchiseptica*. The conjugation was carried out with the use of fresh cultures both of the receiving strain and of the donor strain (*E.coli*) on Bordet-Gengou plates (Bordet-Gengou, *Ann. Inst. Pasteur* (Paris), 23, 415–419, 1909) for at least 6 hours at 35° C. The conjugants were selected on plates of the same medium to which tetracycline (10 μg/ml) and streptomycin (40 μg/ml) had been added (Gross et al., *Proc. Nat'l. Acad. Sci.* USA, 85, 3913–3917, 1988).

B) Analyisis of the CAT activity

The conjugants obtained as described in step A) were grown in 10 ml of Stainer-Scholte medium (Stainer-Scholte, *J. Gen. Microbiol.*, 63, 211–220, 1971) in the presence of 10 μg/ml of tetracycline and 40 μg/ml of streptomycin at 35° C. up to an optical density of 0.7–0.8 at 580 nm.

1 ml of each culture was then centrifuged at 14,000 rpm for 1 minute and the cells were resuspended in 300 μl of 0.25M Tris-HCl, pH 7.8 buffer. The cells were then ruptured by 6 sonication cycles, each of 30 seconds, in a Soniprep 150-HSE device. The lysates were centrifuged in an Eppendorf centrifuge for 10 minutes at 4° C. and the supernatant liquids were recovered, incubated at 65° C. for 8 minutes and centrifuged again.

0.1 μCi of ($C^{14}$) chloramphenicol and 20 μl of 4 mM acetyl coenzyme A were then added to 150 μl of each supernatant liquid, diluted in 0.25M Tris-HCl pH 7.8 buffer and incubated at 37° C. for 1 hour. The reaction was then stopped and the chloramphenicol and its derivatives extracted with 2 ml of cold ethyl acetate 4° C.). The organic phase was evaporated and the various forms of chloramphenicol were separated by thin-layer chromatography with the use of silica plates in a chloroform/methanol mixture (95/5, vol/vol). The plates were then subjected to autoradiography for qualitative evaluation. The quantitative evaluation was effected by the cutting from the plates of the zones corresponding to the two mono-acetylated forms and to the non-acetylated form of chloramphenicol. The radioactivity was then measured by the addition of 4 ml of Dupont ECONOFLUOR TM scintillating liquid.

Figure 9:
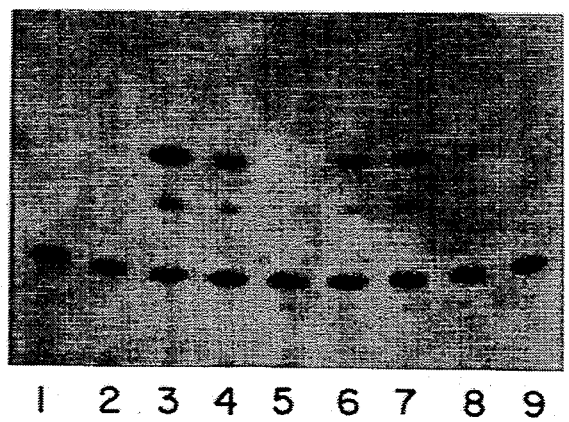

The results are given in FIG. 9. The quantitative analysis showed that the promoter of the fim2 gene directs the synthesis of chloramphenicol acetyl transferase (produced by the CAT gene) very efficiently. If a value of 100% is attributed to the activity of the fim2 gene, the promoters of the fimx gene and of the fim3 gene are 125 times and 3 times weaker than the fim2 promoter respectively.

As regards the promoter of the fim3 gene, although that region was efficient in promoting the transcription of the CAT gene, it was not possible to demonstrate its vir regulation.

This indicated that this promoter was a constitutive promoter.

Example 14

Construction of the Mutants of the Promoter of the fim2 Gene

The 400-bp BamHI-HindIII fragment of the promoter of the fim2 gene was isolated from the plasmid pSM 351. This fragment (10 μg) was then partially digested with 10 units of SpHI at 37° C. for 1 hour so as to produce a BamHI-SphI band of 33 bp. This step was necessary because of the presence of two SphI sites 30 bp apart within the promoter sequence. The deletions affected the remaining 65 bp and were made with the use of synthetic DNA fragments.

Figure 10:
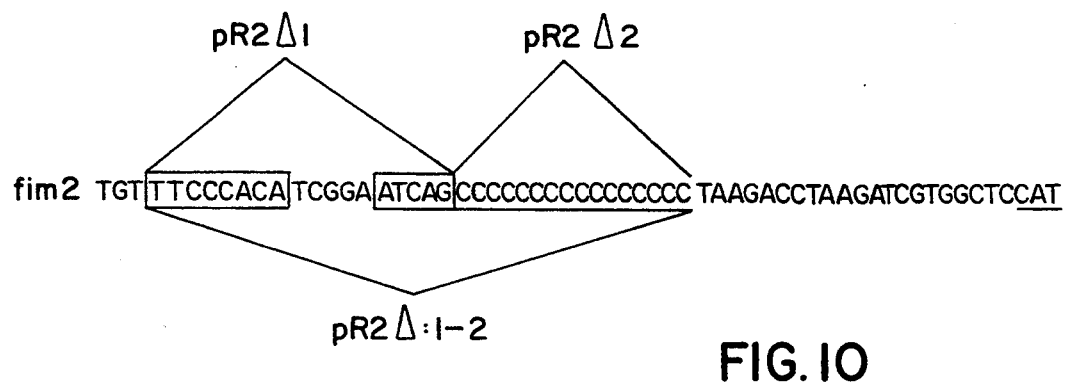
FIG. 10 shows the construction of the mutants of the promoter of the fim2 gene, (SEQ. ID. No: 4)

More precisely, use was made of three double-helix oligonucleotides which had nucleotide sequences corresponding to the segment between the SphI and DdeI restriction sites (the latter being situated within the 65 bp fragment) but were different for each of the desired deletions, as well as one common DdeI-HindIII oligonucleotide (used for the construction of the plasmid pSM 351) which inserted the missing bases necessary in order to return to the original situation in which the transcription-start site (CAT) was followed immediately by a HindIII site. FIG. 10 shows a diagram relating to the deletions made respectively in the "pilinic box" in the "Cs box" and in both boxes. 2 μg of each of the three SphI-DdeI oligonucleotides, representing the three deletions, were ligated with 2 μg of the DdeI-HindIII oligonucleotide in 250 μl of ligation mixture in the presence of 5 units of T4 DNA ligase at 14° C. for one night so as to reconstruct the entire SphI-HindIII sequence less the deleted parts.

The products of the three ligations were purified on 8% acrylamide gel and precipitated with ethanol at −20° C. for one night. These (160 ng) were then ligated separately in 100 μl of ligation mixture to 2 μg of pUC 12, which had previously been digested with 20 units of BamHI and HindIII. The reaction was carried out in the presence of 5 units of T4 DNA ligase at 14° C. for one night. The three resulting ligation products having BamHI-SphI ends were precipitated in the presence of a final concentration of 0.5M of NaClO4 and 0.5 volumes of isopropanol for 15 minutes at ambient temperature (20°–25° C.). 20 ng were then ligated separately with 15 ng of the 330-bp BamHI-SphI fragment. The ligation reactions were carried out as described above and the ligation mixtures were used to transform competent *E.coli* JM 101 cells. The transformants were selected on LB medium to which ampicillin, X-GAL and IPTG had been added. The recombinant plasmids isolated from positive clones with deletions of the "pilinic box", the "Cs box" and both boxes were designated pSM 355, pSM 356 and pSM 357 respectively.

The Bam HI-Hin dIII fragments each containing the promoter region of the fim2 gene with one of the deletions described above were isolated from these three plasmids. 100 ng of each fragment were ligated with 100 ng of the 1630-bp HindIII-XbaI fragment containing the CAT gene without its own promoter and with 200 ng of the plasmid pLA FR2 which had been digested beforehand with BamHI and XbaI (10 units). The ligation mixture was then used to transform competent *E.coli* 5K cells. The transformants were selected on LB medium to which tetracycline (12.5 μg/ml) had been added. The positive clones with the deletion of the "pilinic box" the "Cs box" or both boxes were indicated pR2 Δ1, pRΔ2 and pR2 Δ1-2 respectively. These plasmids were transferred into competent *E.coli* SM 10 cells and then into *B.bronchiseptica* strains 7865 and 7866 by conjugation. The CAT test, carried out on the cell extracts of these strains indicated that none of the three mutants was able to promote the transcription of the CAT gene and thus showed that both boxes are essential.

Example 15

Modulation of the Transcription.

In order to check the modulating effect of the culture conditions on the expression of the heterologous gene placed under the control of the promoter region of fim2, 10 ml of Stainer-Scholte medium (a) and 10 ml of the same medium to which $MgSO_4$ had been added to give a final concentration of 50 mM (b) were inoculated in duplicate with B.bronchiseptica 7865 cells containing the plasmid pR2 and the plasmids including the mutations of the fim2 promoter.

The cultures were kept at 35° C. for one night and then used to inoculate the same medium. At an OD of 0.7 at 580 nm, the cells were treated as described previously to determine their CAT activities.

Figure 11:
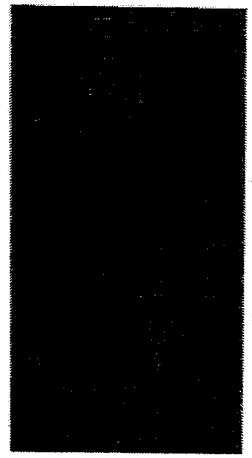
FIG. 11 shows the modulation verification by means of CAT tests carried out on the cell extracts of vir$^+$ B.bronchiseptica transformed by pR2 and grown in the absence (1) and in the presence (2) of MgSO$_4$.

The results, given in FIG. 11, indicated that the promoter of the fim2 gene was subject to modulation and completely lost its activity in the presence of 50 mM $MgSO_4$. The same promoter modified by the deletion of one or both boxes could no longer vary its activity under non-permissive conditions.

---

We claim:

1. An isolated fim3 promoter having the following nucleotide sequence

AAATTCCCACACAACCAT-
CAGCCCCCCCCCCGGACCTGATATT
CTGATGGCCGACGCCAAGCACAT as SEQ.
ID. No. 6.

2. A cloning vector comprising the fim3 promoter of claim 1.

3. A cloning vector according to claim 2, wherein said vector is pSM349 deposited as ATCC 68105.

4. A microorganism transformed by a vector according to claim 2 or claim 3, wherein said microorganism is Bordetella.

5. A microorganism according to claim 4, wherein said Bordetella is selected from the group consisting of *Bordetella pertussis, Bordetella parapertussis* and *Bordetella bronchiseptica*.

6. A recombinant DNA molecule, useful for the expression of a protein of interest in Bordetella, comprising the structural gene which codes for said protein, wherein said gene is positioned in the correct reading arrangement such that expression of said gene is under the control of the fim3 promoter of claim 1.

7. A recombinant DNA molecule according to claim 6, in which the Bordetella is selected from the group consisting of *Bordetella pertussis, Bordetella parapertussis* and *Bordetella bronchiseptica*.

8. A recombinant DNA molecule according to claim 6, in which the structural gene codes for an immunogenic protein of *Bordetella pertussis*.

9. A recombinant DNA molecule according to claim 8, in which the immunogenic protein is selected from the group consisting of: a pilinic subunit, pertussis toxin or subunits thereof, filamentous hemagglutinin, adenylate cyclase and the protein 69K.

10. A recombinant DNA molecule according to claim 6, in which the expression of the structural gene which codes for the protein of interest is constitutive.

11. A strain of Bordetella selected from the group consisting of *Bordetella pertussis, Bordetella parapertussis* and *Bordetella bronchiseptica* transformed with the recombinant DNA molecule according to claims 6, 7, 8, 9 or 10.

* * * * *

UNITED STATES PATENT AND TRADEMARK OFFICE
CERTIFICATE OF CORRECTION

PATENT NO.   : 5,395,764
DATED        : March 7, 1995
INVENTOR(S)  : Barbara Riboli, et al.

It is certified that error appears in the above-identified patent and that said Letters Patent is hereby corrected as shown below:

On the title page, item [75] Assignee, should read--Eniricerche S.p.A.--.

Signed and Sealed this

Twenty-second Day of August, 1995

Attest:

BRUCE LEHMAN

*Attesting Officer*     *Commissioner of Patents and Trademarks*